Figure 1:
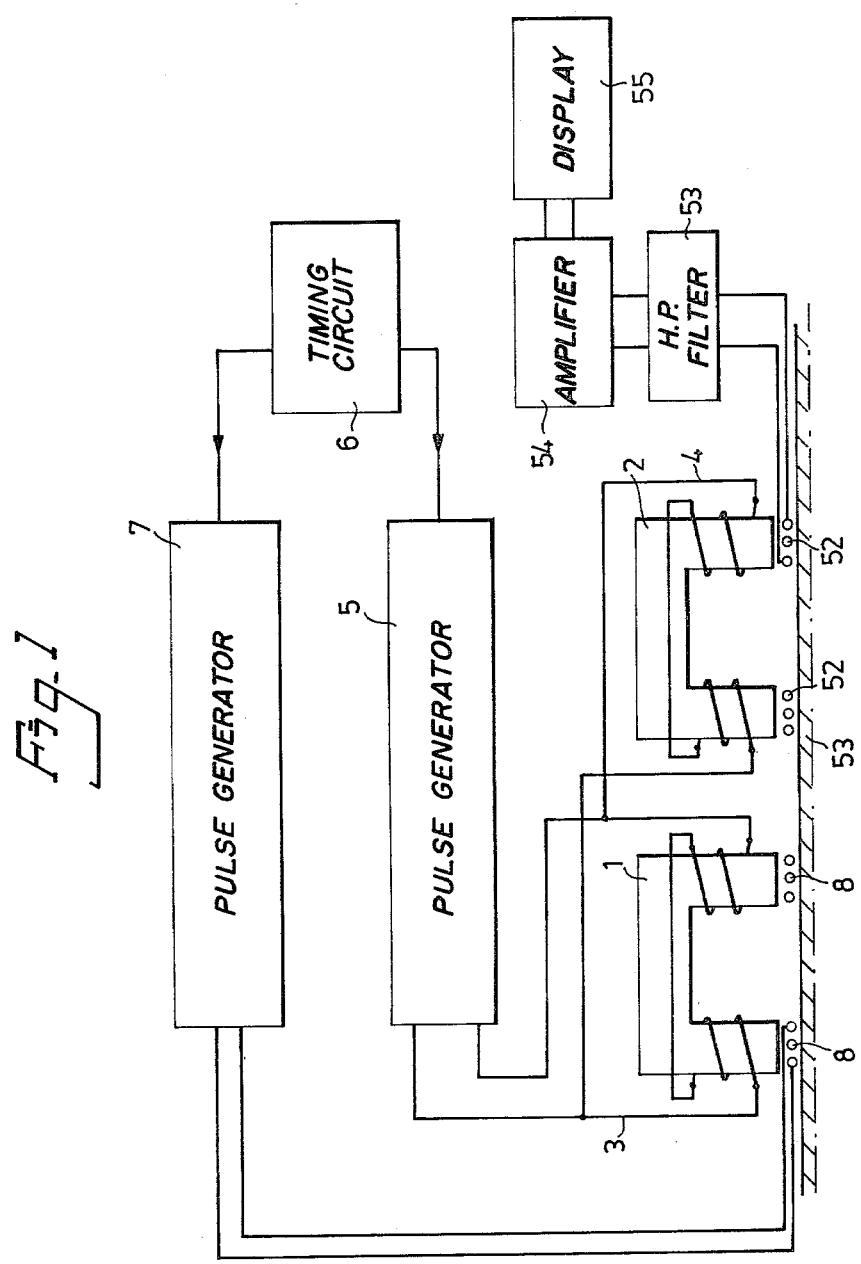

United States Patent [19]

Robinson

[11] 4,307,615

[45] Dec. 29, 1981

[54] METHOD AND APPARATUS FOR TRANSMITTING AND RECEIVING ELECTROMAGNETICALLY GENERATED AND RECEIVED ULTRASONIC PULSES, PRIMARILY AT NON-DESTRUCTIVE TESTING

[75] Inventor: Thomas Robinson, Nyköping, Sweden

[73] Assignee: Studsvik Energiteknik AB, Nyköping, Sweden

[21] Appl. No.: 89,717

[22] Filed: Oct. 31, 1979

[30] Foreign Application Priority Data

Nov. 7, 1978 [SE] Sweden ................................. 7811511

[51] Int. Cl.³ .......................................... G01N 29/04
[52] U.S. Cl. ..................................................... 73/643
[58] Field of Search ......................... 73/643, 627, 632

[56] References Cited

U.S. PATENT DOCUMENTS 4,164,873 8/1979 Böttcher et al. ...................... 73/643

OTHER PUBLICATIONS

Ninth World Conference on Non-Destructive Testing, "Electromagnetic Generation of Ultrasonic Waves in Absence of External Magnetic Field and its Applications to Steel Production Lines," Kawashima et al., 11/79.

Primary Examiner—Anthony V. Ciarlante
Attorney, Agent, or Firm—LeBlanc, Nolan, Shur & Nies

[57] ABSTRACT

A method and an apparatus for transmitting and receiving electromagnetically generated ultra-sound, particularly for non-destructive testing of electrically conductive material, comprising the steps of generating one or more magnetic fields by means of one or more electromagnets (1,2,3,4) and supplying to a transmitter coil (8) in said magnetic field a supersonic frequency, and scanning a receiver coil (52) in said magnetic field. For known apparatuses the signal/noise ratio of a received signal is unfavorable, especially at the testing of non-magnetic material.

According to the present invention said ratio is improved in that said magnetic field is generated during a short time compared with the time between two subsequently occurring magnetic fields, and a pulse well-defined in length of supersonic frequency is supplied to the transmitter coil (8) about or at the maximum strength of the magnetic field or fields.

The receiver coil (52) thereafter is scanned, but also about or at the maximum strength of the magnetic field or fields. The said pulse has a preferred length of one or two complete sinusoidally-shaped cycles, whereafter the signal is cancelled entirely.

According to a preferred embodiment the said pulse is generated through a thyristor-controlled (42) discharge circuit comprising a capacitor (38) and a vacuum gap tube (37). According to a preferred embodiment there is further provided a high-pass filter (53) between the receiver coil (52) and an amplifier (54).

13 Claims, 4 Drawing Figures

METHOD AND APPARATUS FOR TRANSMITTING AND RECEIVING ELECTROMAGNETICALLY GENERATED AND RECEIVED ULTRASONIC PULSES, PRIMARILY AT NON-DESTRUCTIVE TESTING

This invention relates to a method and an apparatus for transmitting and receiving ultrasonic pulses, which are electromagnetically generated and received, primarily in non-destructive tests.

The invention particularly relates to a method, which is especially advantageous for non-destructively testing non-magnetic materials, and to an apparatus for the same purpose.

In electromagnetic ultrasonic tests ultra-sound is introduced non-contactingly into a body of electrically conductive material by means of a strong magnetic field, where a coil in the field is fed with a current of supersonic frequency. The receiver includes a receiving coil in a strong magnetic field, in which coil a signal is generated when the body vibrates with supersonic frequency in the magnetic field of the receiver.

This principle, thus, is well-known. One example of its utilization is defect indication in steel or other electrically conductive material. However, the signal strength received in a receiver is low in relation to the noise level occurring when this technique is used for testing non-magnetic material. For this reason, the technique heretofore has been applied substantially only to the testing of magnetic material where the signal/noise ratio is much more favourable.

The present invention has the object of increasing the signal/noise ratio to such a degree, that the technique advantageously can be used in the non-destructive testing of non-magnetic electrically conductive material. One very important example of utilizing the present invention is the detection of defects in steel workpieces or products in a state heated above the Curie-temperature.

By the method and apparatus according to the invention the signal/noise ratio is improved radically in the testing of both non-magnetic and magnetic material.

The present invention relates to a method of transmitting and receiving electromagnetically-generated ultrasound, especially when non-destructively testing electrically conductive material, comprising the steps of generating one or more magnetic fields by means of one or more electromagnets and supplying a transmitter coil in said magnetic field with a signal of supersonic frequency, and of scanning a receiver coil in said magnetic field. The method is characterized in that said magnetic field is generated by a first pulse generator during a time which is short as compared with the time between two sequentially occurring magnetic fields, that at or about the maximum strength of the magnetic field or fields a pulse of supersonic frequency well-defined in length is generated by means of a second pulse generator and is supplied to said transmitter coil, whereafter the receiver coil is scanned also at or about the maximum strength of the magnetic field or fields, and that said pulse is caused to prevail for a time substantially shorter than said magnetic field.

The invention further relates to an apparatus for transmitting and receiving electromagnetic ultra-sound, especially in non-destructive testing, comprising one or more electromagnets for generating one or more magnetic fields, a transmitter coil and a receiver coil located at the poles each of its own or of the same electromagnet, and means for supplying said electromagnets and transmitter coil with energy. The apparatus is characterized in that said lastmentioned means comprise a first pulse generator capable of supplying energy to one or more electromagnets in the form of a pulse during a time which is short compared with the time between two sequentially occurring pulses, and a second pulse generator capable a short time thereafter, at or about the maximum of the magnetic field or fields generated by the electromagnet or -magnets, of supplying said transmitter coil with a pulse of supersonic frequency having a well-defined length and a duration substantially shorter than the duration of said magnetic field, and scanning means capable after the supply of said lastmentioned pulse to the transmitter coil to scan said receiver coil also at or about the maximum of the magnet field or fields generated by the electromagnet or -magnets.

Figure 2:
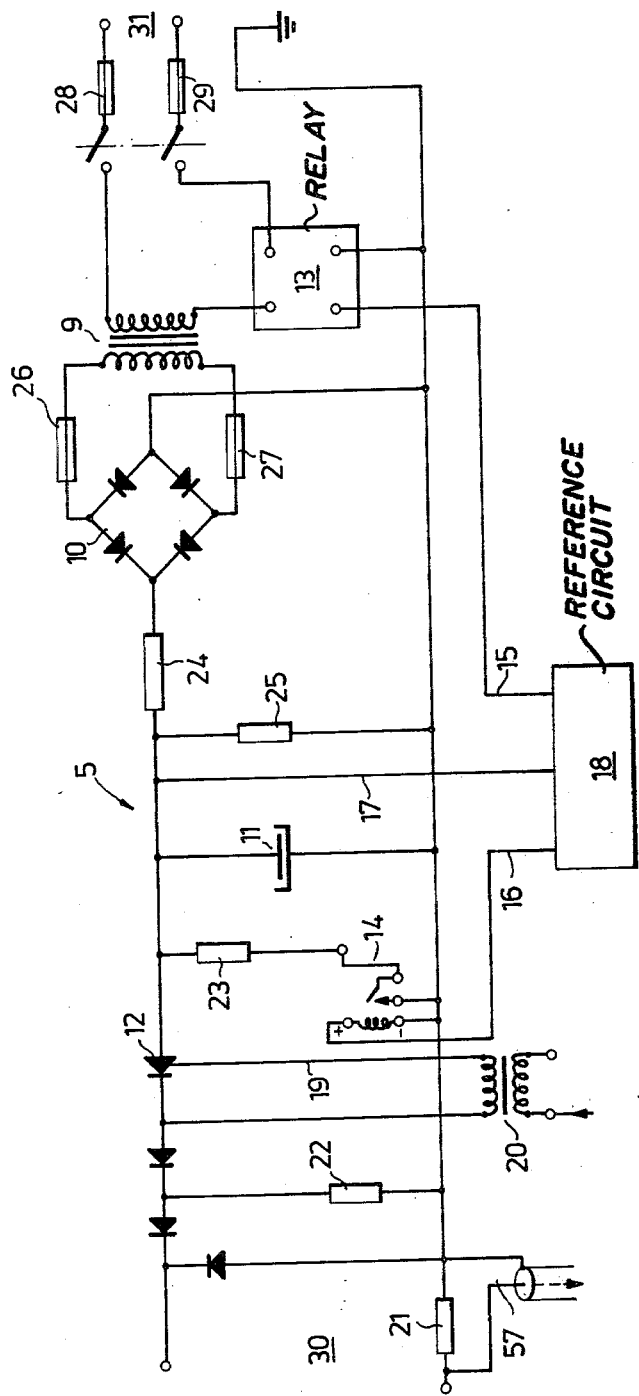
Figure 3:
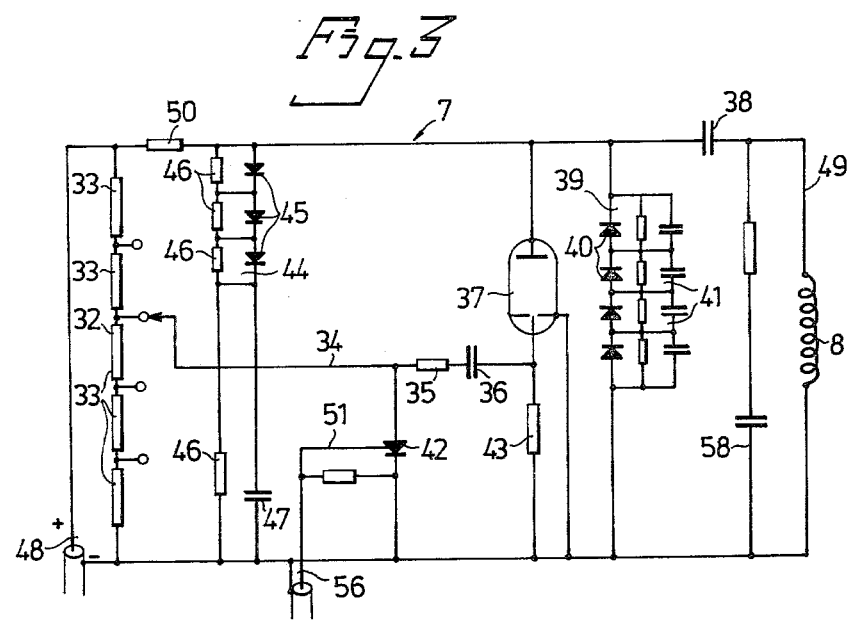
Figure 4:
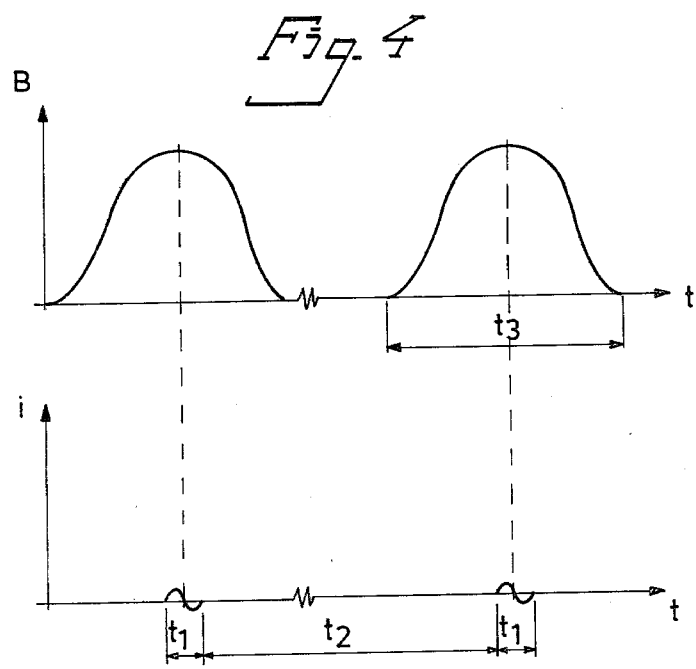

The invention is described in greater detail in the following, with reference to the accompanying drawings, in which FIG. 1 is a block diagram of an apparatus according to the invention, FIG. 2 is a schematic diagram of a preferred embodiment of a pulse generator for an electromagnet, FIG. 3 is a schematic diagram of a preferred embodiment of a pulse generator for a transmitter coil, and FIG. 4 is a curve for the magnetic field strength of the electromagnet and an ultrasonic pulse as a function of time.

In FIG. 1 a first electromagnet 1 is used for transmitting, and a second electromagnet 2 is used for receiving. Both magnets have associated windings 3 and 4, respectively.

The magnet cores of the electromagnets 1,2 preferably are of ferromagnetic material and are so designed, that eddy currents therein are prevented. The magnet cores preferably are laminated, but cores of ferromagnetic powder or threads may also be used.

The windings 3,4 of the electromagnets 1,2 are connected to a first pulse generator 5 which is capable for generating short pulses of very great strength. The pulse length preferably is 0.5–100 ms.

A preferred embodiment of the pulse generator is shown in FIG. 2. The pulse generator is connected to and controlled by a programmed time circuit 6 of a known suitable type.

The said time circuit 6 also is capable of controlling a second pulse generator 7 shown in FIG. 3, which generator is capable of generating pulses of supersonic frequency to a transmitter coil 8. Said coil 8 is so located relative to said first electromagnet 1, that the coil 8 will be within the magnetic field from the first electromagnet 1.

According to a preferred embodiment the transmitter coil 8 is designed as an endless track as, such as a runner track seen from above, the straight portions of which are located beneath the poles of the magnet core 1.

The first pulse generator 5, shown in FIG. 2, comprises a transformer 9, a diode rectifier 10, a capacitor 11 or capacitor circuit with great capacitive reactance, for example 10 mF, and a thyristor 12. There are further provided two relays 13,14, from which conductors 15,16, together with a conductor 17 connected after the rectifier 10 are connected to a reference circuit 18 shown by way of a block. Said reference circuit 18 is capable of evaluating the pulse length and charging of the capacitor 11, and consists of a suitable known circuit.

The control conductor 19 of said thyristor 12 is connected to said time circuit 6 via a transformer 20. There are further provided resistances 21–25 and fuses 26–29 of different strength. The output 30 is connected directly to the windings 3,4 of the electromagnets 1,2, and the input 31 is connected to a voltage source, preferably mains voltage.

The windings of the electromagnets are connected in parallel to the first pulse generator 5. They may instead be connected in series, and they may also be fed from separate units. The function of the circuit shown in FIG. 2 follows. While charging the capacitor 11 with direct voltage from the rectifier 10 the thyristor 12 is blocked. After the charging a control pulse is emitted from the time circuit 6 to the thyristor 12 via the conductor 19. The capacitor 11 thereby is discharged through the windings 3,4 of the electromagnets 1,2. Thereafter the capacitor 11 again is charged, followed by a new discharge, a.s.o.

The second pulse generator 7, shown in FIG. 3, comprises a variable voltage divider 32 consisting of resistance 33, from which a conductor 34 is connected to a switch element, such as a vacuum gap tube 37, via a resistance 35 and a capacitor 36. Said generator further comprises a main capacitor 38 or capacitor circuit and a shunt circuit 39 consisting of diodes 40 and RC-circuits 41. A thyristor 42 together with the resistance 35, capacitor 36 and an additional resistance 43 constitute a discharge circuit for igniting the trigger electrode of the vacuum gap tube 37.

There is further provided a circuit 44, consisting of diodes 45, resistances 46 and a capacitor 47 for attenuating voltage tops over the vacuum gap tube 37 and shunt circuit 39.

In parallel with the transmitter coil 8 is an RC-circuit 58 which is tuned to attenuate frequencies above said supersonic frequency.

The input 48 to the circuit is connected to a direct voltage source with high voltage, for example 1500 volt, and the output 49 is connected directly to said transmitter coil 8.

The function of the second pulse generator 7 is in principle as follows.

The capacitor 38 is charged completely through a resistor 50. The capacitor 47 simultaneously is charged to the same voltage, and the capacitor 36 is charged to a voltage given by said voltage divider. A short pulse via the control conductor 51 of the thyristor 42 opens the same, whereby the capacitor 36 is discharged and thereby gives rise to a negative voltage on the trigger electrode of the vacuum gap tube 37. Thereby the tube 37 is ignited, whereby the capacitor 38 is discharged through the transmitter coil 8, whereafter the inductance in the coil 8 again charges the capacitor 38 with inverted polarity. The capacitor 38 thereafter is recharged to its original polarity through the shunt circuit 39 and the coil 8, but when this re-charging is completed further re-chargings can be prevented if the vacuum gap tube 37 again has received its blocking capacity, i.e. when it does not ignite through. The shunt circuit 39 is blocked and, therefore, the signal is completely cancelled. Thus, a complete sinusoidal wave has been generated, whereafter no current flows through the transmitter coil 8. As is evidently clear, a short and very well-defined pulse of supersonic frequency is obtained.

The embodiment of the second pulse generator described above by way of example comprises a vacuum gap tube. Alternatively, other switch elements, such as a relay, a thyristor or other semiconductor components, e.g. gas-discharge tubes, can be applied. The invention, therefore, must not be regarded as being restricted to the utilization of a vacuum gap tube.

The supersonic frequency here referred to is below 2 MHz, preferably 50 kHz to 500 kHz.

By a suitably chosen break-down voltage for the vacuum gap tube 37 and minor suitable changes of the circuit in general, every pulse can be caused to comprise a plurality of complete sinusoidally-shaped cycles and also only half a cycle. The vacuum gap tube 37 a.o. is hereby adjusted to the capacitor 38 so that the capacitor 38 has a voltage sufficiently high for igniting the vacuum gap tube more than one time. The pulse generator shown in FIG. 3 is only one embodiment and, therefore, the invention must not be regarded as being restricted to an embodiment where only a complete cycle is generated.

According to a preferred embodiment, one to two complete cycles are generated.

A receiver coil 52 is located beneath the second electromagnet 2 in the same manner and preferably with the same configuration as the transmitter coil 8.

Current pulses in the transmitter coil 8 induce a similar varying current in the surface layer of the test material 53.

When a magnetic field B exists in a conductor, and a current I simultaneously flows in the conductor (i.e. the test material), a force F, so-called Lorentz-force, is formed on the conductor equal to $F = 1 \times B$, where 1 has the dimension $A/m^2$ and B Tesla.

In the present case the force oscillates with supersonic frequency, whereby thus ultra-sound is introduced into the test material. When the ultra-sound after having been reflected arrives at the receiver 2,4,52, the ultrasonic waves, according to Faraday's induction law, generate a corresponding electromotoric force, which yields a varying signal in the receiver coil 52.

This received signal passes through a high-pass filter 53 in order to eliminate components with low frequency. The signal thereafter is amplified in an amplifier 54, and the result then is processed and/or illustrated in a unit 55 intended for this purpose, for example a data processing unit and/or an oscilloscope or the like.

The above description refers to an arrangement with two electromagnets 1,2. For certain applications, however, only one electromagnet can be used, at which the transmitter coil and the receiver coil are provided.

In known ultrasonic techniques using electromagnetic ultrasound the emitted pulses are of an undefined length, due to the formation of a tail after the pulse proper. The tail length generally is such as to influence the receiver during the time the receiver is intended to receive reflections from the pulse proper. This implies a high noise level and/or interference level. In the case of testing non-magnetic material, the known technique implies such a high noise level that the signal proper hardly can be distinguished.

In many cases, however, it is not sufficient to emit a pulse with a well-defined length, because the magnetic fields from the electromagnets are not sufficiently strong. The reason for this is that an electromagnet emitting a sufficiently strong magnetic field is complicated to cool, partially due to its greatest permissible dimension and to the environment in which the testing takes place. One example of such testing is the testing of steel above the Curie-temperature, i.e. when the steel is non-magnetic. Furthermore, cooled electromagnets with associated cooling arrangements are relatively expensive.

According to the present invention, a pulsed magnetic field is generated, the duration of which is short in relation to the time between the magnetic field pulses, during the maximum of which a well-defined ultrasonic pulse is emitted and received. Under these circumstances the signal/noise level is increased very substantially.

Due to the fact that the pulsed magnetic field has a short duration, for example 5 ms, at a pulse repitition of 10 per second, very strong magnetic fields can be formed without giving rise to an appreciable heating of the electromagnets.

The electromagnets 1,2 according to the invention are air-cooled. Compressed air from a suitable known compressed-air unit (not shown) is caused to flow about the magnet core.

In FIG. 4 two diagrams with the same time scale are shown in a schematic manner. The upper diagram shows the magnetic field strength B of the electromagnets as a function of the time, and the lower diagram shows the current i through the transmitter coil as a function of the time.

The time $t_1$ is substantially shorter than the time $t_3$. The time $t_3$ is substantially shorter than the time $t_2$.

The following time intervals can be mentioned by way of example: $0.5\ \mu s \leq t_1 \leq 100\ \mu s$, $50\ ms \leq t_2 \leq 2000\ ms$, $0.5\ ms \leq t_3 \leq 100\ ms$. Typical values preferably are $t_1 = 10\ \mu s$, $t_2 = 500\ ms$ and $t_3 = 10\ ms$.

When the aforesaid times are applied, it is ensured that emission of a pulse is fully completed before a reflected ultrasonic wave is received. It also is ensured that the ultrasonic wave is cancelled before the next emission takes place. Furthermore, the reception takes place at or about the maximum of the magnetic field.

The apparatus operates briefly as follows.

The time circuit 6 emits a pulse to the first pulse generator 5 via the transformer 20, whereby the electromagnets 1,2 generate said magnetic field. Hereafter a pulse is emitted from the time circuit 6 to the second pulse generator 7 via its trigger input 56 to the thyristor 42, whereby one or more complete sinusoidally-shaped cycles are fed to the transmitter coil 8. The lastmentioned pulse is emitted at or about the maximum of the magnetic field. The ultrasonic wave generated in the test material is reflected against a defect or a wall and after reflection gives rise to a signal in the receiver coil 52. This signal is evaluated and/or illustrated.

The time circuit 6 can be designed in known manner to emit pulses in a predetermined time order, or it can be designed so as to emit the pulse to the first pulse generator 5 in a predetermined time order and to emit the pulse to the second pulse generator 7 when the magnetic field or fields have obtained the strength intended. In the latter case the strength of the magnetic field can be read from a signal from an output 57 from the first pulse generator 5, see FIG. 2. The programmed time circuit 6 may also include a suitable data processing equipment, from which different sequences of pulses are controlled.

By the present invention, where a magnetic field B is generated during a short time $t_3$ during which a substantially shorter pulse $t_1$ with well-defined length of supersonic frequency is emitted and received, the signal/noise ratio is increased substantially, and at the same time the demand of cooling the electromagnet or -magnets is small in spite of high effects applied. The invention, thus, provides a simpler method and a simpler apparatus for utilizing electromagnetic ultra-sound than heretofore has been possible.

The present invention, of course, can be modified without abandoning the invention idea. The structure of the pulse generators, for example, can be changed. One or more electromagnets can be used. The transmitter coil and the receiver coil may be the same, in which case a switch means is provided between the high-pass filter and, respectively, the second pulse generator and the coil for switching from transmitting to receiving.

The invention, thus, must not be regarded restricted to the embodiment described above, but can be varied within the scope of the attached claims.

The present invention has been exemplified by ultrasound reflected in the material, but can be used also in the case that the ultra-sound is transmitted through the test material.

I claim:

1. A method of transmitting and receiving electromagnetically generated and received pulses of ultrasound, primarily for non-destructive testing of electrically conductive material, especially steel with a temperature above the Curie-temperature, comprising the steps of generating one or more magnetic fields by one or more electromagnets (1, 2, 3, 4) where each magnetic field is generated in the form of pulses by a first pulse generator (5) and where each magnetic field pulse has a duration that is short as compared with the time interval between two successively occurring magnetic field pulses, characterized in that a tailess ultrasonic pulse of well-defined length is developed in said material by conducting an electrical current pulse through a transmitter coil (8) in one of the magnetic fields at or about the maximum magnetic field strength, that thereafter a signal resulting from the ultrasonic pulse is received at a receiver coil (52) in one of said magnetic fields, that said receiver coil is scanned also at or about maximum magnetic field strength for said signal, that said current pulse is conducted through said transmitter coil only for a time that is substantially shorter than each magnetic field pulse, and that said current pulse is generated by a second pulse generator (7) and consists of at least one or a plurality of cycles of a sinusoidal wave.

2. A method as defined in claim 1, wherein a programmed time circuit (6) emits a first pulse to said first pulse generator (5) to generate said magnetic field, and thereafter emits an additional second pulse to said second pulse generator (7) to generate said current pulse, where said second pulse is emitted at or about the maximum magnetic field strength.

3. A method as defined in claim 2, characterized in that said first pulse activates a thyristor (12) in the first pulse generator (5), and a capacitor (11) or capacitor circuit with high capacitive reactance is caused to be discharged through the winding or windings (3, 4) of said electromagnet or -magnets (1, 2).

4. A method as defined in claim 2, characterized in that said second pulse activates a thyristor (42) in the second pulse generator (7), and that a capacitor (38) or capacitor circuit is caused to be discharged through the transmitter coil (8) via a switch element, such as a vacuum gap tube (37), whereafter the capacitor (38) is caused to be discharged through the transmitter coil (8) via a shunt circuit (39) comprising diodes (40), and that the capacitor (38) again one or more times is discharged via the vacuum gap tube (37) and thereafter the shunt circuit (39), provided that the voltage of the capacitor (38) is sufficiently high to be conducted via the vacuum gap tube (37).

5. A method as defined in claim 2, characterized in that the magnetic field pulses each have a duration of 0.5 ms to 100 ms, preferably 10 ms, and that said current pulse to the transmitter coil (8) has a duration of 0.5 μs to 100 μs, preferably 10 μs.

6. A method as defined in claim 1 wherein a reflection of each ultrasonic pulse is received by the receiver coil, wherein each current pulse is completed before reception of the reflected ultrasonic pulse, and wherein each reflected ultrasonic pulse is received before the next current pulse is supplied to the transmitter coil.

7. A method as defined in claim 1, there being a plurality of current pulses which are supplied in time-spaced relation to said transmitter coil for developing a corresponding plurality of ultrasonic pulses, the duration of each magnetic field pulse being less than the time interval between successively occurring ones of the current pulses.

8. An apparatus for generating and receiving pulses of ultrasound primarily for non-destructive testing of electrically conductive material, comprising one or more electromagnets (1, 2, 3, 4) for generating a corresponding number of magnetic fields, a transmitter coil (8) located in one of said fields, a receiver coil (52) located in one of said fields, a first pulse generator (5) for supplying energy to each electromagnet in the form of time-spaced pulses each having a duration that is short as compared with the time interval between successively occurring ones of said time-spaced pulses, and a second pulse generator (7) for supplying an electrical current pulse of supersonic frequency to said transmitter coil at or about the maximum strength of each of the magnetic fields to develop a tailless ultrasonic pulse of pre-selected length in said material, said current pulse having a duration which is substantially shorter than each magnetic field and consisting of at least one or a plurality of cycles of a sinusoidal wave, said ultrasonic pulse being effective to develop a signal in said receiver coil, and means (54,55) for sensing reception of said signal by said receiver coil at or about the maximum strength of each magnetic field after the said current pulse is supplied to said transmitter coil.

9. An apparatus as defined in claim 8 wherein a programmed timing circuit (6) emits a first pulse to said first pulse generator (5) to cause said first generator to deliver energy to the electromagnet (1,2,3,4) or -magnets and thereafter emits an additional second pulse to said second pulse generator (7) to causes said second generator to generate said current pulse, said timing circuit (6) emitting said second pulse a certain predetermined time after the first pulse.

10. An apparatus as defined in claim 8 wherein said first pulse generator (5) includes a thyristor (12), which is connected into a circuit closed with a capacitor or capacitor unit (11) and the winding (3, 4) or windings of said electromagnet (1, 2) or -magnets, wherein the thyristor (12) upon the emission of said first pulse from the timing circuit assumes conductive state, and the capacitor (11) is discharged through the winding or windings (3, 4).

11. An apparatus as defined in claim 8 characterized in that the second pulse generator (7) comprises a switch element, such as a vacuum gap tube (37), and a capacitor (38) or capacitor circuit in series with said transmitter coil (8), and a shunt circuit (39) including a diode circuit directed to the conductance direction of the vacuum gap tube (37), that preferably a thyristor (42) is provided and capable in its conductive state of activating the trigger electrode of the vacuum gap tube (37) so that the tube ignites, and that upon the emission of said second pulse from the timing circuit (6) the capacitor (38) is discharged via the vacuum gap tube (37) and transmitter coil (8) and thereafter via the shunt circuit (39) and transmitter coil (8), whereafter the capacitor (38) again is discharged one or several times via the vacuum gap tube (37) and thereafter the shunt circuit (39), provided that the voltage of the capacitor (38) is sufficiently high to be conducted via the vacuum gap tube (37).

12. An apparatus as defined in claim 1, characterized in that two electromagnets (1,2) are provided, the windings of which are connected in parallel or in series to the first pulse generator (5), and that the transmitter coil (8) is provided at one electromagnet (1), and the receiver coil (52) at the second one (2).

13. An apparatus as defined in claim 1, characterized in that a high-pass filter (53) is provided between the receiver coil (52) and an amplifier (54) in order to filter off components of low frequency in the signal received.

* * * * *

UNITED STATES PATENT AND TRADEMARK OFFICE
CERTIFICATE OF CORRECTION

PATENT NO. : 4,307,615
DATED : December 29, 1981
INVENTOR(S) : Thomas Robinson

It is certified that error appears in the above-identified patent and that said Letters Patent is hereby corrected as shown below:

Column 1, line 26, "However, the signal strength" should begin a new paragraph.

Claim 12, column 8, line 38, "claim 1" should be -- claim 8 --.

Claim 13, column 8, line 44, "claim 1" should be -- claim 8 --.

Signed and Sealed this

Sixth Day of November 1984

[SEAL]

Attest:

Attesting Officer

GERALD J. MOSSINGHOFF

Commissioner of Patents and Trademarks